(12) United States Patent
Turturro et al.

(10) Patent No.: US 10,697,482 B2
(45) Date of Patent: Jun. 30, 2020

(54) ACCESSORY CLAMP HAVING A ROD CLAMP AND AN ACCESSORY INTERFACE

(71) Applicant: Medline Industries, Inc., Northfield, IL (US)

(72) Inventors: Michael Turturro, Arlington Heights, IL (US); Matthew Kruse, Arlington Heights, IL (US); Stacey Kiefer, Antioch, IL (US)

(73) Assignee: Medline Industries, Inc., Northfield, IL (US)

( * ) Notice: Subject to any disclaimer, the term of this patent is extended or adjusted under 35 U.S.C. 154(b) by 0 days.

(21) Appl. No.: 16/236,859

(22) Filed: Dec. 31, 2018

(65) Prior Publication Data

US 2019/0136883 A1    May 9, 2019

Related U.S. Application Data

(62) Division of application No. 14/244,209, filed on Apr. 3, 2014, now Pat. No. 10,190,609.

(51) Int. Cl.
| | |
|---|---|
| *F16B 2/10* | (2006.01) |
| *F16M 13/02* | (2006.01) |
| *A61B 90/57* | (2016.01) |
| *F16B 45/00* | (2006.01) |

(52) U.S. Cl.
CPC ............... *F16B 2/10* (2013.01); *A61B 90/57* (2016.02); *F16M 13/022* (2013.01); *A61B 2090/571* (2016.02); *F16B 45/00* (2013.01); *F16M 2200/02* (2013.01)

(58) Field of Classification Search
CPC .... F16B 2/10; F16B 45/00; F16B 2/02; F16B 2/12; A61B 90/57; A61B 2090/571; A61B 2019/267; A61B 2019/268; A61B 19/26; F16M 13/022; F16M 2200/02; F16L 3/10; F16L 3/1008; F16L 3/1016; F16L 3/1025; F16L 3/1041; F16L 3/105; F16L 3/1075; F16L 3/1083; F16L 3/1091
USPC ....................................................... 248/230.4
See application file for complete search history.

(56) References Cited

U.S. PATENT DOCUMENTS

| | | | | |
|---|---|---|---|---|
| 3,503,580 A | | 3/1970 | Erwin | |
| 3,537,150 A | * | 11/1970 | John | F16B 12/42 403/344 |
| 4,355,922 A | * | 10/1982 | Sato | E04G 7/16 248/229.11 |
| 4,382,416 A | | 5/1983 | Kellogg-Smith | |
| 4,953,819 A | * | 9/1990 | Davis | A61M 5/1415 211/107 |
| 5,806,819 A | | 9/1998 | Martone | |

(Continued)

*Primary Examiner* — Christopher Garft
(74) *Attorney, Agent, or Firm* — Fitch, Even, Tabin & Flannery LLP (57) ABSTRACT

An accessory clamp for use with a rod includes an accessory interface and a corresponding rod clamp. The accessory interface includes at least one of at least one accessory hook and at least one accessory T-slot. By one approach, at least one of the accessory hooks comprises a pivoting accessory hook. By one approach the rod clamp can comprise a universal rod clamp. As one example in these regards, the universal rod clamp can include a selectively variable gripping surface to accommodate a variety of rod diameters. By one approach the accessory interface and the corresponding rod clamp can pivot with respect to one another.

8 Claims, 8 Drawing Sheets

(56) References Cited

U.S. PATENT DOCUMENTS

| | | | |
|---|---|---|---|
| 6,119,992 | A | 9/2000 | Stuart |
| D617,451 | S | 6/2010 | Hampton |
| D617,452 | S | 6/2010 | Hampton |
| D631,152 | S | 1/2011 | Hampton |
| D634,004 | S | 3/2011 | Hampton |
| D645,145 | S | 9/2011 | Hampton |
| D646,961 | S | 10/2011 | Hampton |
| 8,443,472 | B2 | 5/2013 | Sherman |
| 10,190,609 | B2 | 1/2019 | Turturro |
| 2006/0278783 | A1* | 12/2006 | Rubin ........................ G09F 7/18 248/230.1 |
| 2007/0278358 | A1* | 12/2007 | Clark .................. B60R 16/0215 248/74.1 |
| 2008/0011907 | A1 | 1/2008 | Jacobsma |
| 2008/0203245 | A1* | 8/2008 | Clark ................... F16L 3/1033 248/68.1 |
| 2010/0123063 | A1* | 5/2010 | Bauchet ............... A47B 96/067 248/274.1 |
| 2016/0161341 | A1 | 6/2016 | Yumoto |

\* cited by examiner

FIG. 1

PRIOR ART

FIG. 10

ACCESSORY CLAMP HAVING A ROD CLAMP AND AN ACCESSORY INTERFACE

CROSS-REFERENCE TO RELATED APPLICATIONS

This application is a divisional of prior U.S. patent application Ser. No. 14/244,209 filed, Apr. 3, 2014, now U.S. Pat. No. 10,190,609, which is incorporated herein by reference in its entirety.

TECHNICAL FIELD

These teachings relate generally to accessory clamps for use with rods.

BACKGROUND

Accessory clamps for use with rods are known in the art. The rods in question are typically cylinders that comprise a part of, for example, IV poles, bed frames and side rails, and so forth. Accessory clamps typically include a rod clamp that permits the accessory clamp to be affixed to the rod. An accessory interface as comprises a part of the accessory clamp is thereby rendered available for local use. Various accessory interfaces are known, including hooks (to hold, for example, bags of fluids to be dispensed into a patient and/or bags to collect fluids being collected from the patient) and so-called accessory T-slot's.

Unfortunately, there is no universal standard governing the size of rods in medical services application settings. IV poles, for example, are available in a wide variety of diameters, with even individual manufacturers offering a variety of diameters within their own product lines. In addition, telescoping IV poles each inherently present two or more rods having different diameters. That said, as a general rule the aforementioned rod clamps as comprise a part of available accessory clamps are typically designed to work with only a single predetermined rod diameter. The few available exceptions in these regards that offer an adjustable rod clamp tend to be bulky, tedious to employ, and overly reliant upon the technician's strength and dexterity to ensure a secure attachment.

Available accessory clamps also tend to be very application specific. As a result, prior art accessory clamps are often ill suited for use with a wide variety of different accessories.

BRIEF DESCRIPTION OF THE DRAWINGS

The above needs are at least partially met through provision of an accessory clamp having a rod clamp and an accessory interface described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, an accessory clamp for use with a rod includes an accessory interface and a corresponding rod clamp. By one approach the accessory interface includes at least one of at least one accessory hook and at least one accessory T-slot. As an illustrative example in these regards, a given accessory interface can include two accessory hooks and one accessory T-slot. By one approach, at least one of the accessory hooks comprises a pivoting accessory hook (having, for example, a pivoting range of at least 90° though perhaps no more than 300°).

By one approach the rod clamp can comprise a universal rod clamp. As one example in these regards, the universal rod clamp can include a selectively variable gripping surface to accommodate a variety of rod diameters. By one approach, the selectively variable gripping surface comprises a selectively movable gripping surface to accommodate the variety of rod diameters. Such a universal rod clamp can further include a latch that is separate and discrete from the selectively movable gripping surface and that is configured to lock the universal rod clamp in place on the rod. By one approach the universal rod clamp can further include an adjustment interface by which the aforementioned selectively movable gripping surface is selectively moved.

As another example in these regards, the aforementioned selectively variable gripping surface can include a pair of gripping arms that pivot with respect to one another. Each of these gripping arms can include at least a first and second rod-receiving recess and wherein these rod-receiving recesses are sized differently from one another to thereby accommodate a variety of rod diameters. An adjustable latch can again serve to lock the gripping arms in place on a rod.

These teachings are highly flexible in practice and will accommodate a wide variety of modifications. As but one example in these regards, the accessory clamp can further include an articulated joint that pivotally connects the accessory interface to the rod clamp. So configured, the accessory interface can be rotated to assume a useful orientation in a given application setting. Depending upon the degree of allowed rotation, such an approach permits the accessory clamp to be successfully used with various rods having any of a variety of deployed orientations in a given application setting, including vertical orientations, horizontal orientations, and various orientations between those two orientations.

Such an accessory clamp, depending upon the particular configuration employed, can accommodate any of a wide variety of rod diameters (or even a variety of cross-sectional form factors) and/or any of a variety of accessories. By providing an articulated joint to pivotally connect the accessory interface to the rod clamp, such an accessory clamp can also well accommodate any of a wide variety of rod orientations and application settings. These teachings can be economically implemented and can help avoid the need for a wide variety of specifically-sized clamps and/or specifically-targeted accessory interfaces even in an application setting, such as a hospital, where a wide variety of differently-sized and/or oriented rods are typically expected.

Figure 1:
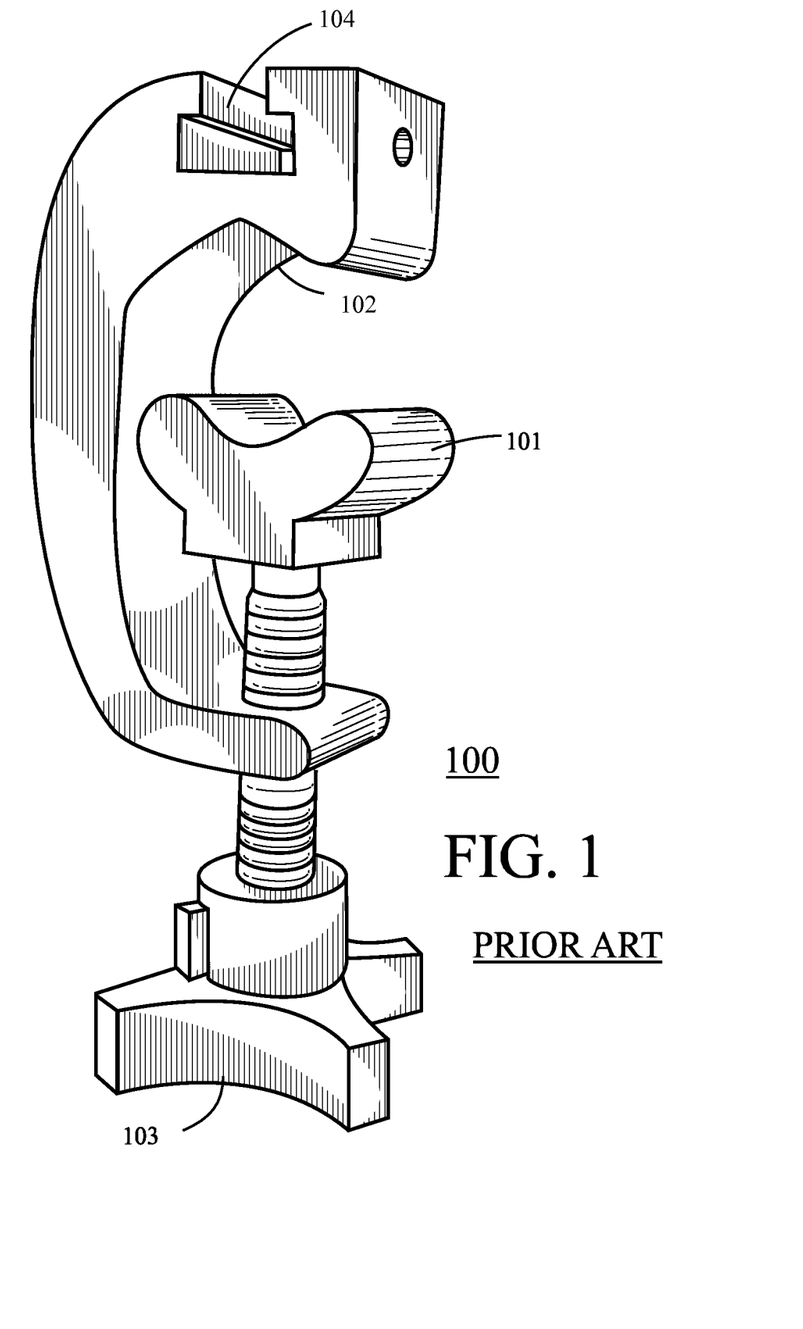
FIG. 1 comprises a perspective view as configured in accordance with the prior art.

These and other benefits may become clearer upon making a thorough review and study of the following detailed description. First, however, it may be useful to provide additional information regarding a not-untypical accessory clamp that offers a universal rod clamp. In particular, the prior art accessory clamp 100 as shown in FIG. 1 includes a selectively movable gripping surface 101 that can be selectively moved back and forth with respect to an opposing gripping surface 102 by manipulation of a rotatable handle 103. While such an accessory handle will indeed accommodate many differently-sized rods, such an approach can be inconvenient during use and, worse yet, may require strength and/or dexterity beyond what the technician possesses to sufficiently secure to a given rod. In addition, this accessory clamp 100 includes only a single accessory interface 104 (in this case, an accessory T-slot as is known in the art).

Figure 2:
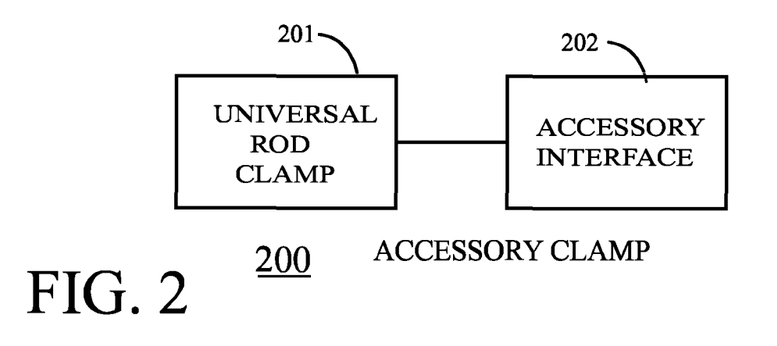
FIG. 2 comprises a schematic representation as configured in accordance with various embodiments of these teachings.

Referring now to FIG. 2, the present teachings contemplate an accessory clamp 200 for use with a rod, wherein the accessory clamp 200 can include a universal rod clamp 201 that operably couples to an accessory interface 202. The accessory interface can include at least one of one or more accessory hooks (such as, for example, IV bag hooks or urine bag hooks) and/or at least one accessory T-slot.

By one approach the aforementioned universal rod clamp includes both a selectively variable gripping surface to thereby accommodate a variety of rod diameters and a latch that is separate and discrete from the selectively variable gripping surface and that is configured to lock the universal rod clamp in place on the rod. By one approach the selectively variable gripping surface comprises a selectively movable gripping surface that can accommodate a variety of rod diameters sizes. By another approach the selectively variable gripping surface comprises a pair of gripping arms that pivot with respect to one another, wherein each of the gripping arms includes at least a first and second rod-receiving recess and wherein the first and second rod-receiving recesses are sized differently from one another to thereby accommodate differently-sized rod diameters. More specific examples in all these regards are provided further herein.

Figure 3:
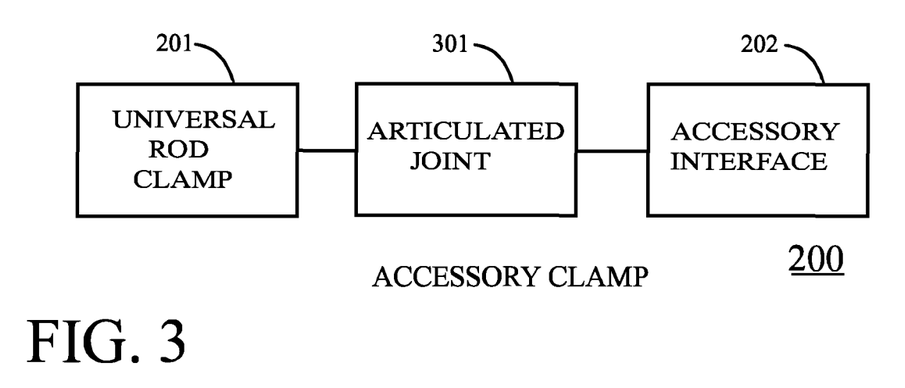
FIG. 3 comprises a schematic representation as configured in accordance with various embodiments of these teachings.

With reference to FIG. 3, the accessory clamp 200 can further include an articulated joint 301 that pivotally connects the accessory interface 202 to the universal rod clamp 201. By one approach this articulated joint 301 is biased towards a particular orientation through the use of a biasing mechanism (such as one or more springs, camming surfaces, and so forth). Furthermore, if desired, this articulated joint 301 can be biased towards more than one particular orientation such that the articulated joint 301 can be biased to selectively retain any of a plurality of specific orientations (for example, two or more orientations that are 90° removed from one another).

Such an accessory clamp 200 can readily adapt for successful use with a variety of rods having any of a variety of cross-sectional diameters and/or deployed orientations in a given application setting (such as a vertical orientation, a horizontal orientation, or some angle therebetween). By employing both a selectively variable gripping surface and a separate and discrete latch, such an accessory clamp 200 can be readily securely fastened to a rod without requiring undue manipulation and/or strength on the part of the technician who installs the accessory clamp 200 in place.

Figure 4:
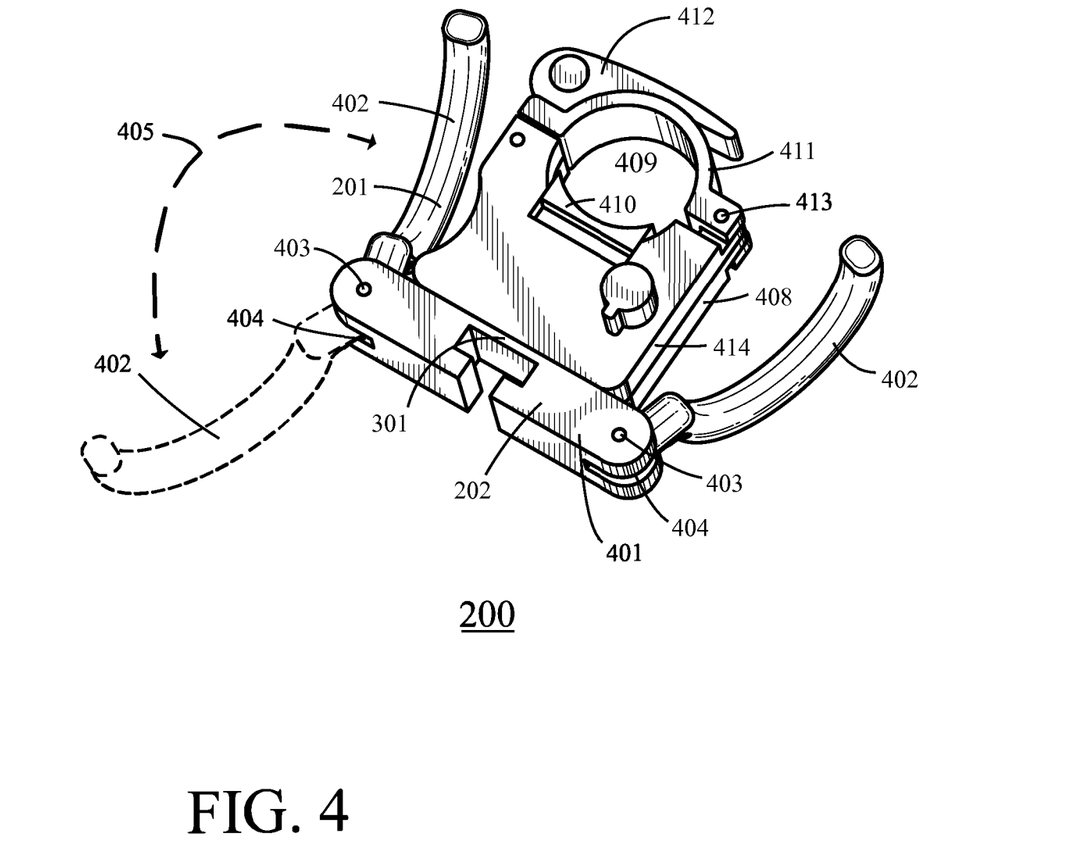
FIG. 4 comprises a perspective view as configured in accordance with various embodiments of these teachings.
Figure 5:
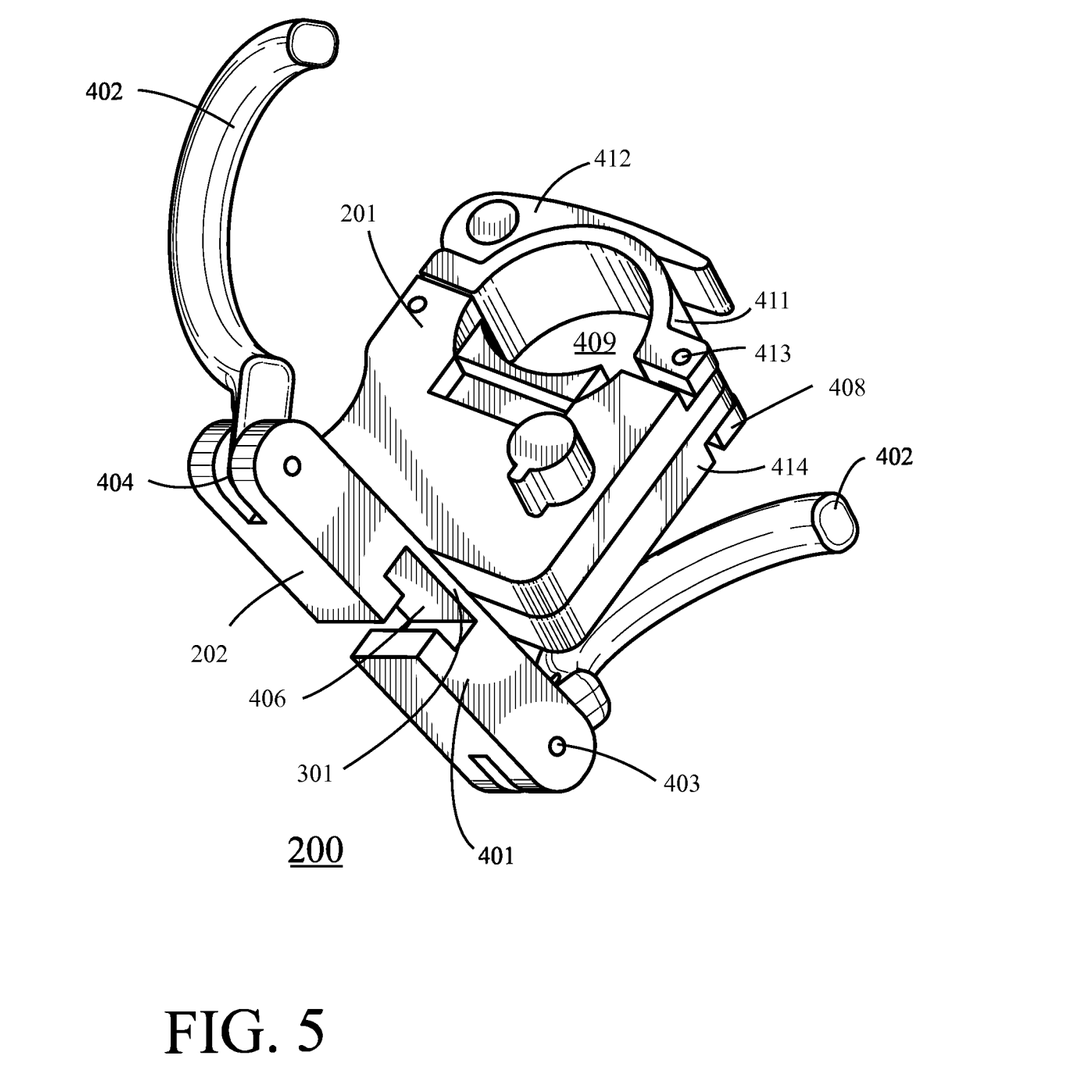
FIG. 5 comprises a perspective view as configured in accordance with various embodiments of these teachings.

Referring now to FIGS. 4 and 5, further details regarding a particular instantiation of an accessory clamp 200 will be presented. In this example, the accessory interface 202 comprises a beam 401. A pair of accessory hooks 402 are pivotally connected at opposing ends of the beam 401 by a corresponding pin 403. Each end of the beam 401 includes a slot 404 formed therein to provide a track that guides the pivoting of each hook 402.

The range of pivotability for each accessory hook 402 can be limited as desired via such a slot 404. As indicated by the arrow denoted by reference numeral 405, in this example each accessory hook 402 can pivot through a range of somewhat more than 180° (for example, about 200°). That range of pivotability can of course vary with the needs of a particular application setting, with a useful pivoting range typically being at least 90° but no more than about 300°.

In this example, the slot 404 that permits and guides the above-described pivoting action of the accessory hooks 402 is parallel to the longitudinal axis of the beam 401. Other orientations may be useful in some application settings for one or both accessory hooks 402 as desired.

In this example the accessory interface 202 also includes an accessory T-slot 406 formed therein. Accessory T-slots are well known in the art and comprise a T-shaped channel that will accommodate a corresponding T-shaped component on a given accessory. In this example the accessory T-slot 406 is disposed perpendicular to the longitudinal axis of the beam 401. Again, other orientations can serve as desired. Also in this example the accessory T-slot 406 is centrally located with respect to the beam 401 and again other locations can be accommodated as desired. Depending upon the size of the beam 401, these teachings will also accommodate having two or more accessory T-slots if desired.

These teachings will accommodate using any of a variety of materials for the above described components. Metal and/or any of a variety of plastics, for example, can serve well in these regards.

In this example the universal rod clamp 201 includes a main body 408 that facilitates providing a rod gripping area 409. In these regards the main body 408 includes a selectively movable gripping surface 410 that can be moved in and out of the main body 408 as described in more detail below. If desired, this gripping surface 410 can have a textured surface (such as, for example, a knurled surface) to serve as an enhanced gripping surface. These teachings will also accommodate having a second material disposed on the gripping surface 410 such as a soft plastic or rubber material. Such materials can serve to enhance gripping capability and/or to help protect the cosmetic appearance of the rod's external surface.

A pivoting arm 411 connects to the main body 408 via a pin 413. A latch 412 in turn serves to lock the pivoting arm 411 in place to thereby lock the universal rod clamp 201 in place on a rod of choice. In this example the universal rod clamp 201 also includes an adjustment interface 414 by which the aforementioned selectively movable gripping surface 410 is selectively moved in and out of the main body 408 to thereby appropriately size the rod gripping area 409.

Figure 6:
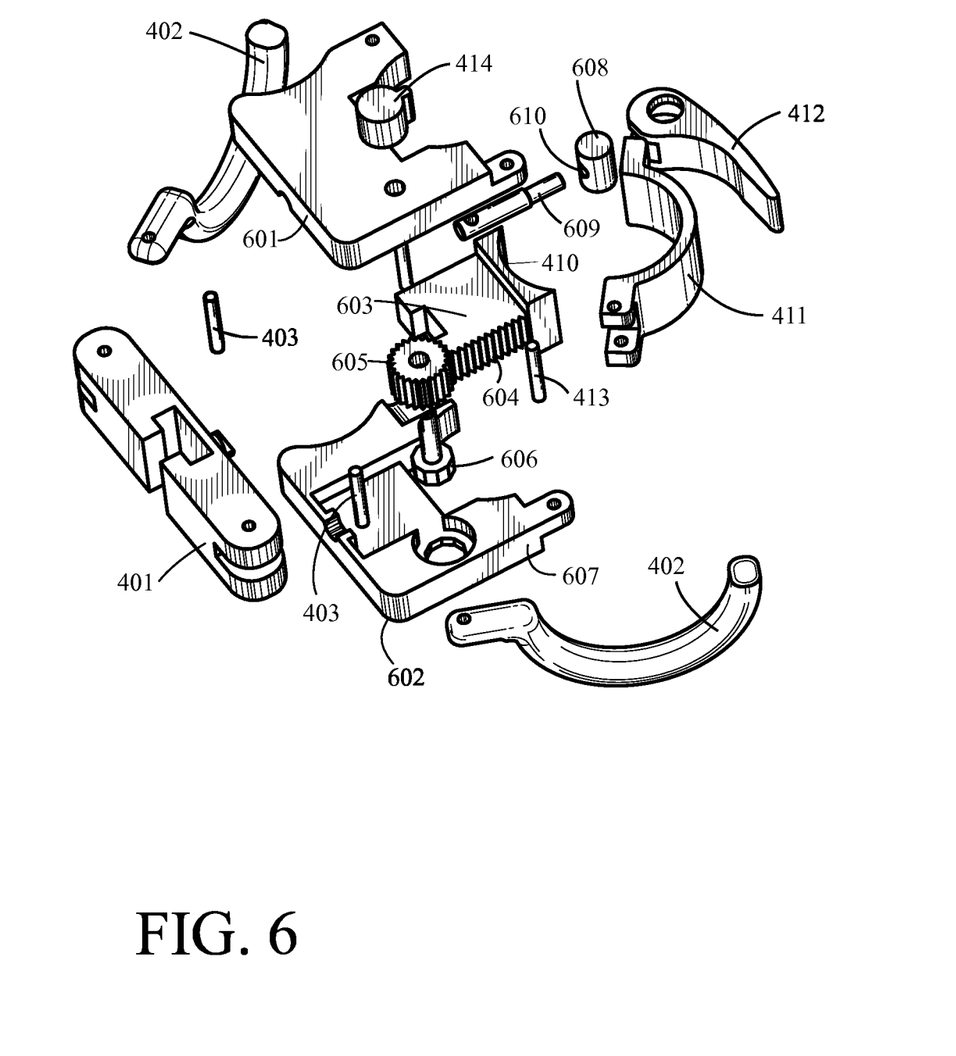
FIG. 6 comprises an exploded perspective view as configured in accordance with various embodiments of these teachings.

Referring to FIG. 6, the main body 408 in this example comprises a first portion 601 and a second portion 602. Each of these portions generally comprises one half of the main body 408. So configured, these two portions of the main body 408 can internally accommodate various components that facilitate the selective movement of the selectively movable gripping surface 410.

More particularly, the selectively movable gripping surface 410 (which includes a rounded concave portion well suited to gripping engagement with the rounded exterior of a rod) integrally connects to a block 603. This block 603, in turn, has teeth 604 formed along one edge thereof. These teeth 604 are configured to engage a gear 605 that couples in turn to the aforementioned adjustment interface 414 that comprises, in this example, a user-manipulable knob.

So configured, rotation of the user manipulable knob will cause corresponding rotation of the gear 605. Rotation of the gear 605, in turn, will cause corresponding movement of the aforementioned block 603 and hence the selectively movable gripping surface 410. Rotating the user manipulable knob in one direction will cause the selectively movable gripping surface 410 to move outwardly of the main body 408 and hence the selectively movable gripping surface 410 will further constrict the rod gripping area 409. Conversely, rotating the user manipulable knob in the opposite direction will cause the selectively movable gripping surface 410 to move inwardly of the main body 408 and hence further open the rod gripping area 409 to thereby accommodate a larger-sized rod.

In this example, the aforementioned gear 605 also attaches to a lock component 606. In this example the lock component 606 has an octagonally-shaped cross-section. The second portion 602 of the main body 408 further includes in this example an octagonally-shaped well 607 that is sized, located, and otherwise configured to conformally receive that lock component 606. So configured, when the lock component 606 is received within the well 607, the lock component 606 cannot rotate and hence the gear 605 cannot rotate.

In this example, a user can unlock the above-described mechanism by pulling the adjustment interface knob outwardly from the main body 408 to thereby disengage the lock component 606 from the well 607. With the lock mechanism disengaged, the user can then turn the knob to appropriately position the selectively movable gripping surface 410. The user can then push the knob back towards the main body 408 to thereby place the lock component 606 into the well 607 to thereby lock the gear 605 and hence lock the selectively movable gripping surface 410 in place.

So configured, the aforementioned lock can only lock the selectively movable gripping surface 410 at specific positions; i.e., those positions that correspond to when the aforementioned lock component 606 is appropriately aligned with the well 607 such that the lock component 606 can be received therein. If desired, and referring momentarily to FIGS. 7 and 8, the exterior surface of the main body 408 can include markings 701 to identify the specific locations where such alignment occurs and hence where the selectively movable gripping surface 410 can be locked at a particular position.

Figure 7:
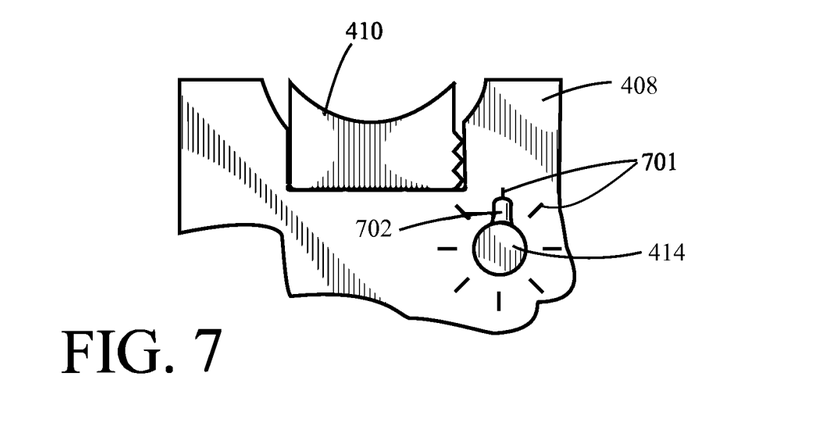
FIG. 7 comprises a top plan detail view as configured in accordance with various embodiments of the invention.
Figure 8:
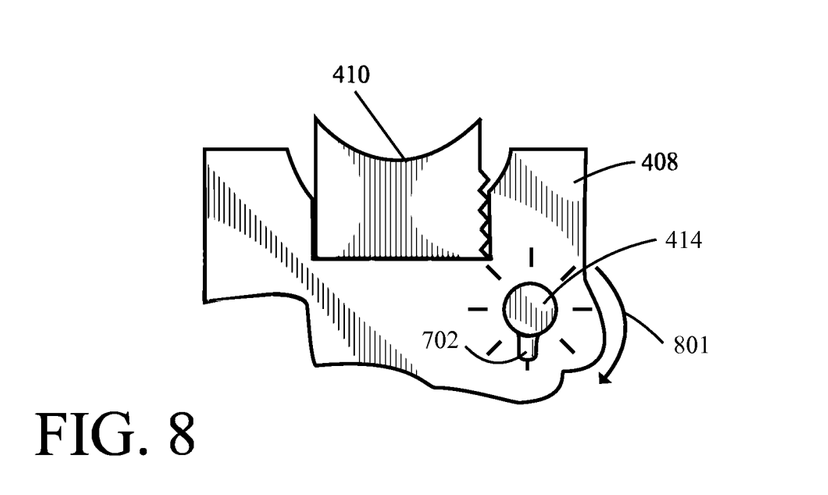
FIG. 8 comprises a top plan detail view as configured in accordance with various embodiments of these teachings.

Those markings 701 can be formed by, for example, printing the markings 701 on the main body 408 and/or by forming those markings 701 as a part of the main body 408 (for example, as indentations or as raised, embossed content). In this example, where the locking mechanism is based upon an octagon, these positions are equally spaced from one another and hence the aforementioned markings 701 are similarly equally spaced from one another. Also if desired, and as illustrated in these examples, the user interface 414 can include a tab 702 or other pointer or indicator to thereby facilitate aligning the rotational position of the adjustment interface 414 with the aforementioned markings 701.

So configured, by rotating the adjustment interface 414 from the position shown in FIG. 7 to the position shown in FIG. 8 (as represented by the arrow denoted by reference numeral 801) the selectively movable gripping surface 410 is moved outwardly of the main body by a specific corresponding distance. Accordingly, a user can readily, easily, and intuitively move the selectively movable gripping surface 410 to a specific location as desired. By one approach, further markings may be included on the main body 408 as correspond to rods having particular specific dimensions.

Referring again to FIGS. 4 and 5, the universal rod clamp 201 and the accessory interface 202 are pivotally connected to one another by way of an articulated joint. FIG. 5, for example, illustrates the two aforementioned components having been rotated 90° with respect to one another as compared to the orientation shown in FIG. 4. In this example the articulated joint is biased towards the two orientations shown in FIG. 4 and FIG. 5 (using, for example, spring biased ball-and-detent components as are known in the art) to thereby help retain these components in either of these two orientations as desired.

Referring again to FIG. 6, the aforementioned latch 412 in this example is physically separate and discrete from the selectively movable gripping surface 410. That is to say, the latch 412 is a separate physical component from the selectively movable gripping surface 410. In this example the latch 412 can selectively pivot about a corresponding pin 608. This pin 608, in turn, interacts with a lateral pin 609 via a hole 610 formed through a side of the pin 608. The latch 412, when selectively pivoted about the aforementioned pin 608, makes contact with the aforementioned pivoting arm 411. Continued pivoting causes force to be applied to the pivoting arm 411 by virtue of the off-centered orientation of the pin 608 in the latch 412 and the restraining force of the lateral pin 609 that secures the latch 412 to the body of the clamp. This force compresses the pivoting arm 411 into the rod, and simultaneously compresses the rod into the gripping surface 410, thus attaching the clamp to the rod. When fully engaged, the latch 412 lays adjacent to the pivoting arm 411. To release the clamp from the rod, the latch 412 is selectively pivoted in the reverse direction until it disengages from the pivoting arm 411.

Figure 9:
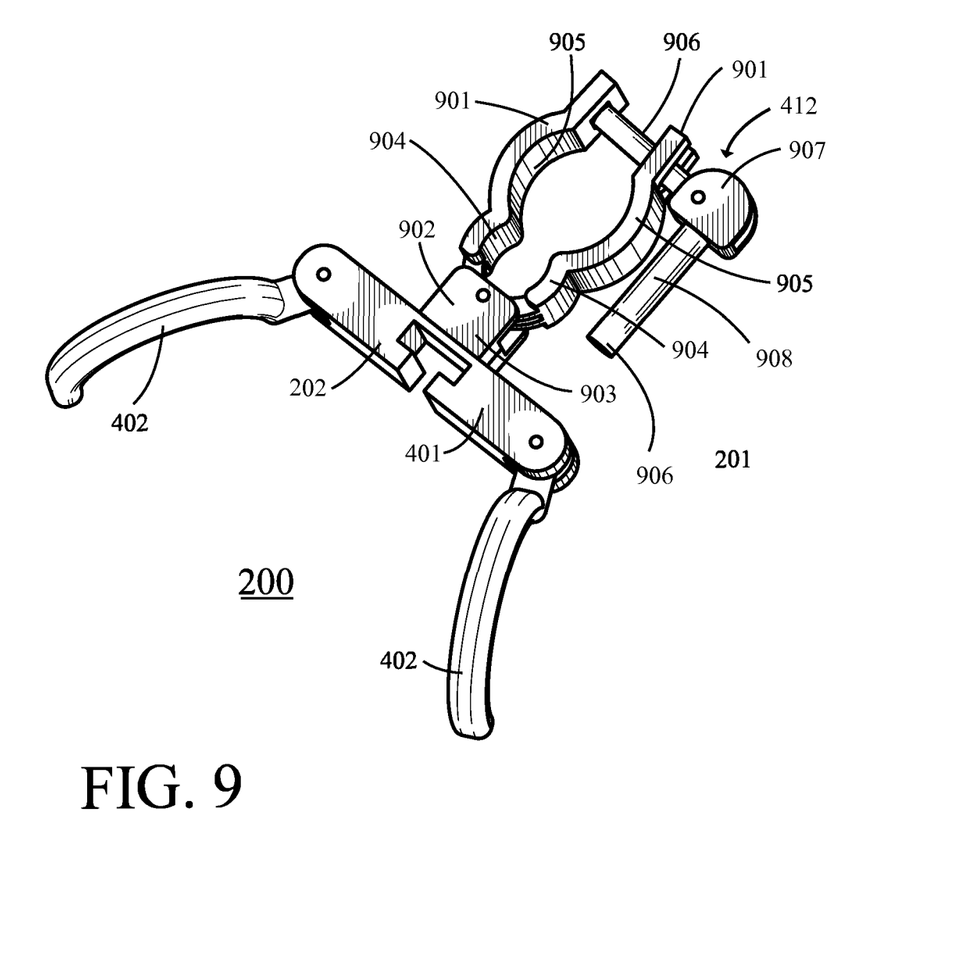
FIG. 9 comprises a perspective view as configured in accordance with various embodiments of the invention.
Figure 10:
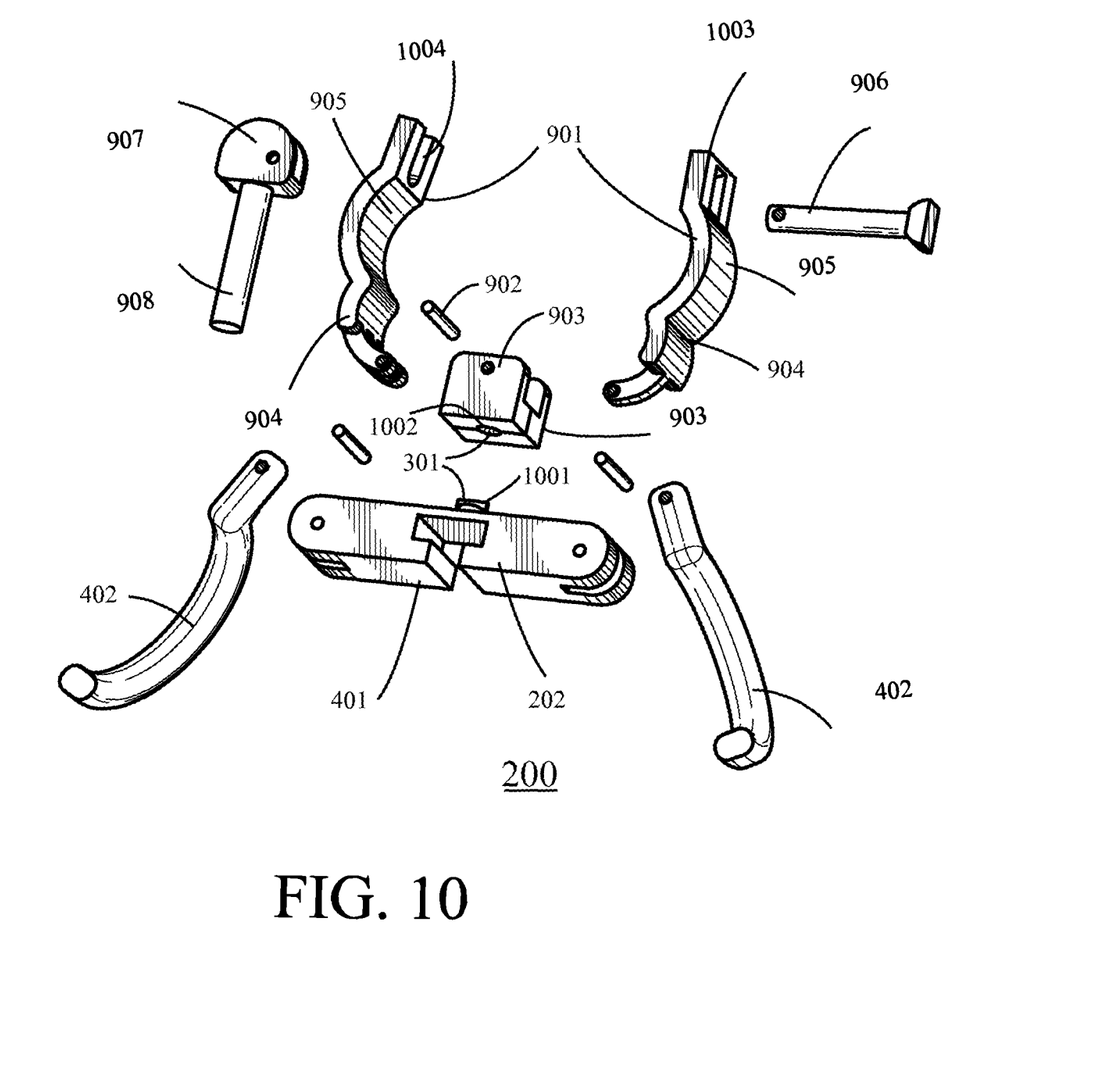
FIG. 10 comprises an exploded perspective view as configured in accordance with various embodiments of these teachings.

As noted previously, these teachings are highly flexible in practice and will accommodate numerous variations and modifications. FIGS. 9 and 10 provide some examples in these regards. In these illustrations the universal rod clamp 201 comprises selectively variable gripping surfaces that include a pair of gripping arms 901 that pivotally connect via a pin 902 to a bracket 903. So configured, the gripping arms 901 can pivot away from or towards each other as desired.

In this example the gripping arms 901 each include a first rod-receiving recess 904 and a second rod-receiving recess 905. These rod-receiving recesses comprise rounded, concave indentations in the interior face of each gripping arm 901. As shown, these two rod-receiving recesses 904 and 905 are sized differently from one another to thereby accommodate different rod diameters. In particular, the rod-receiving recess 904 that is positioned closer to the pivot point is of smaller extent and size than the second rod-receiving recess 905. Accordingly, the smaller rod-receiving recesses 904 can be used in combination with one another to grip a relatively smaller-sized rod while the second rod-receiving recesses 905 can be used in combination with one another to grip a relatively larger-sized rod.

In this illustrative example the gripping arms 901 each include two rod-receiving recesses. These teachings will readily accommodate providing three or more differently-sized rod recesses if desired. Also in this illustrative example, the rod-receiving recesses present a smooth face for contacting the exterior surface of the rod. If desired, these rod-receiving recesses can have a textured surface (such as, for example, a knurled surface) to serve as an enhanced gripping surface. These teachings will also accommodate having a second material disposed on the rod-receiving recesses such as a soft plastic or rubber material. Such materials can serve to enhance gripping capability and/or to help protect the cosmetic appearance of the rod's external surface.

With continued reference to FIGS. 9 and 10, the rod clamp in this example includes a member 906 that fits through a hole 1003 in a first one of the gripping arms 901 and a slot 1004 in the other of the gripping arms 901. In this illustrative example the hole 1003 is designed such that the member 906 can pivot back and forth in a rocking style motion. This makes it easier to fit that member 906 into the slot 1004. A latch 907 receives the end of that member 906 and pivotally connects thereto. In this example the latch 907 pivotally connects to that member 906 at an eccentric off-axis location. So configured, by pushing a corresponding handle 908 that comprises a part of the latch 907 towards the corresponding gripping arm 901 (as shown in FIG. 9) the use of the gripping arms 901 are locked in a secured position vis-à-vis one another (presuming placement of the gripping arms 901 around a corresponding rod).

The articulated joint 301 illustrated in FIG. 10 includes a pin that extends outwardly of the accessory interface 202 and that features a corresponding cap 1001 at the outer end thereof. The above-described bracket 903 in this example includes a corresponding hole 1002 to receive that pin. In this example that bracket 903 comprises two halves that each share one half of the aforementioned hole 1002. By bringing these 2 halves of the bracket 903 together around the pin, the aforementioned pin will be disposed within the hole 1002 and the cap 1001 will prevent the pin from being removed therefrom. At the same time, however, the accessory interface 202 can rotate about that pin with respect to the bracket 903.

Such an accessory clamp offers great convenience in a typical application setting that includes a variety of differently-sized rods and/or differently-oriented rods (including application settings where different such rods come and go in ordinary course and hence even the differences can change from day to day). In particular, by providing a universal rod clamp that utilizes a selectively variable gripping surface in order to accommodate a variety of rod diameters in conjunction with a latch that is separate and discrete from that selectively variable gripping surface, the rod clamp can be readily and easily appropriately sized for use with a particular rod and then secured to that rod without requiring the physical strength and/or dexterity that typifies the use of prior art accessory clamps. (As used herein, this reference to "universal" will be understood to not necessarily presume compatible use with any rod regardless of its size. Instead, this reference to being "universal" will be understood to refer to an ability to compatibly accommodate a wide variety of presently-available yet differently-sized rods.)

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An accessory clamp for use with a rod, comprising:
   an accessory interface having:
      at least one pivoting accessory hook having a pivoting range of at least 90° but no more than 300°;
      at least one accessory T-slot; and
      a bracket; and
   a universal rod clamp that is operably coupled to the accessory interface and having:
      a pair of gripping arms that pivot with respect to one another about a pin that connects to the bracket, wherein each of the gripping arms includes at least a first and second rod-receiving recess wherein each of the rod-receiving recesses comprises a rounded, concave indentation formed in an interior face of the corresponding gripping arm and wherein the first and second rod-receiving recesses are sized differently from one another to thereby accommodate a variety of rod diameters;
      an adjustable latch that is configured to lock the gripping arms in place on the rod.

2. An accessory clamp for use with a rod, comprising:
   an accessory interface that includes a bracket;
   a universal rod clamp that is operably coupled to the accessory interface and having:
      a pair of gripping arms that pivot with respect to one another about a pin that connects to the bracket, wherein each of the gripping arms includes at least a first and second rod-receiving recess and wherein the first and second rod-receiving recesses are sized differently from one another to thereby accommodate a variety of rod diameters;
      an adjustable latch that is configured to lock the gripping arms in place on the rod.

3. The accessory clamp of claim 2 wherein the accessory interface includes at least one of:
   at least one accessory hook; and
   at least one accessory T-slot.

4. The accessory clamp of claim 3 wherein the accessory interface includes at least both of:
   the at least one accessory hook; and
   the at least one accessory T-slot.

5. The accessory clamp of claim 4 wherein the accessory interface includes at least two of the at least one accessory hook.

6. The accessory clamp of claim 5 wherein at least one of the accessory hooks comprises a pivoting accessory hook.

7. The accessory clamp of claim 5 wherein the at least two of the accessory hooks each comprise a pivoting accessory hook.

8. The accessory clamp of claim 7 wherein the pivoting accessory hooks each have a pivoting range of at least 90° but no more than 300°.

* * * * *